United States Patent [19]

Lasswell

[11] 4,141,360
[45] Feb. 27, 1979

[54] MENSTRUAL EXTRACTION DEVICE

[76] Inventor: Tull C. Lasswell, 626 Oxford Oaks Ct., Oxford, Mich. 48051

[21] Appl. No.: 764,419

[22] Filed: Jan. 31, 1977

[51] Int. Cl.² .............................................. A61M 1/00
[52] U.S. Cl. .................................................... 128/276
[58] Field of Search .............. 128/276, 277, 278, 251, 128/284, 343, 303.11, 342, 245, 341

[56] References Cited

U.S. PATENT DOCUMENTS

| 381,622 | 4/1888 | Healey | 128/251 X |
|---|---|---|---|
| 1,502,503 | 7/1924 | Hollrigl | 128/285 |
| 2,087,511 | 7/1937 | Gould | 128/242 |
| 2,522,108 | 9/1950 | Flagg | 128/276 |
| 3,506,010 | 4/1970 | Murr | 128/276 |
| 3,774,612 | 11/1975 | Marco | 128/304 |
| 3,860,001 | 1/1976 | Levin | 128/276 |
| 4,033,338 | 7/1977 | Igwebike | 128/276 X |

Primary Examiner—Stephen C. Pellegrino
Assistant Examiner—Michael H. Thaler
Attorney, Agent, or Firm—Hauke and Patalidis

[57] ABSTRACT

A vaginal suction apparatus for use particularly during menstrual flow. The device is in the form of a hollow elongated member, having a rounded end portion, defining an inner collection chamber provided proximate the rounded end portion with a screened aperture positionable in the vagina for engagement with the cervix of the uterus. The chamber is closed at its rear end by a wall having a passageway placing the chamber in communication with a suction source, such that by application of suction to the chamber and to the vaginal canal the contents of the uterus are suctioned through the screened aperture into the chamber. Preferably, the rear end wall is removable for emptying the contents of the chamber and for cleaning the chamber.

By use of the device of the invention a method is provided for regulating and shortening menstrual flow.

25 Claims, 9 Drawing Figures

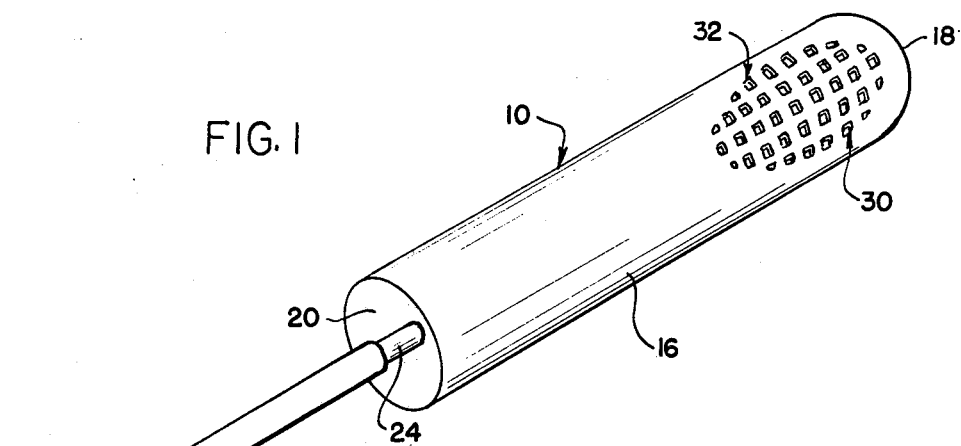
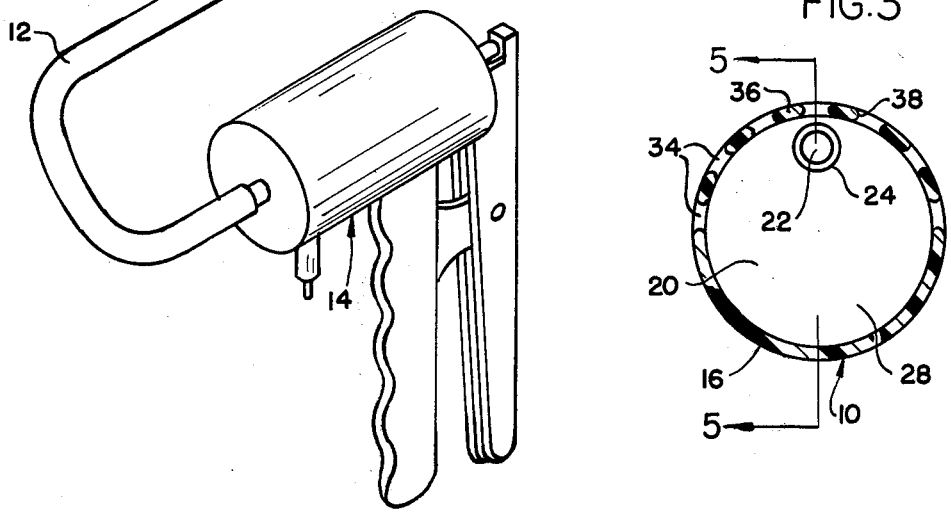
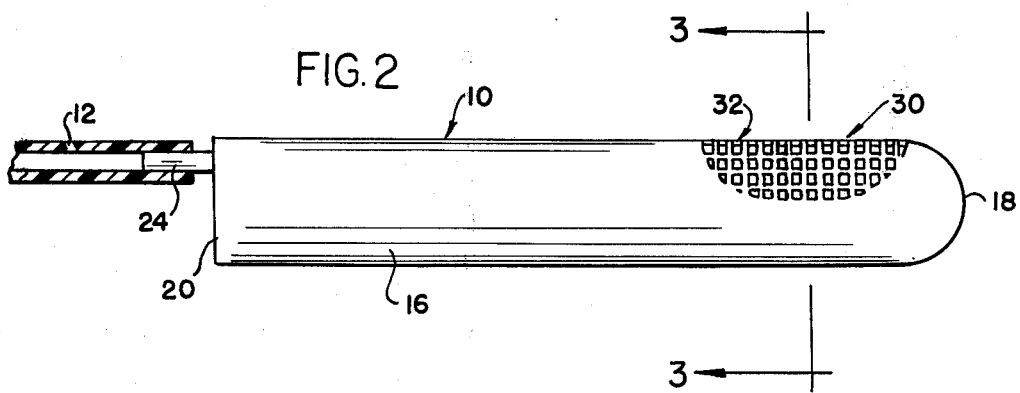
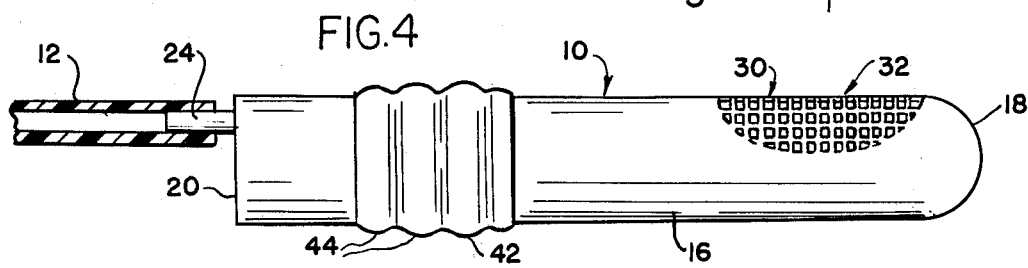

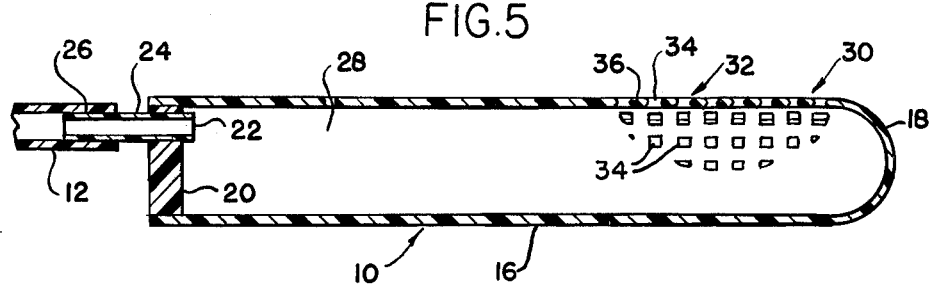
FIG. 5
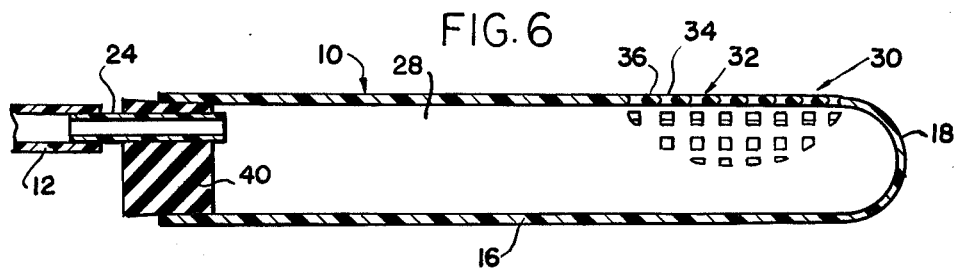
FIG. 6
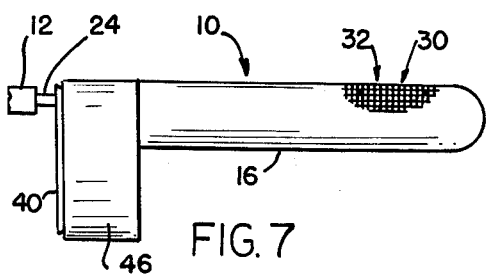
FIG. 7
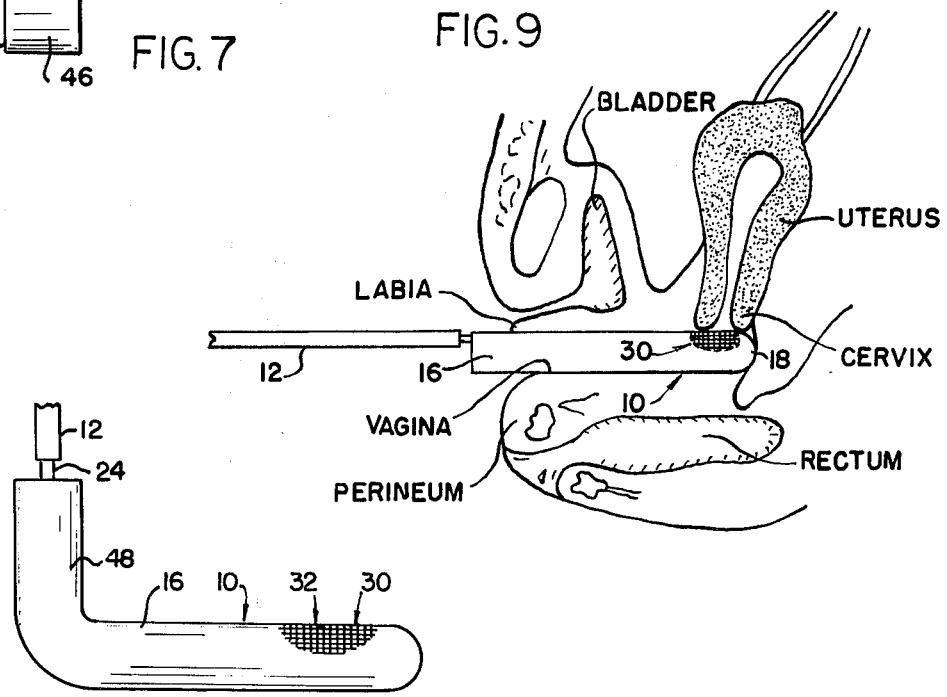
FIG. 9
FIG. 8

MENSTRUAL EXTRACTION DEVICE

BACKGROUND OF THE INVENTION

The invention relates generally to the field of vaginal suction devices, particularly useful during menstrual flow periods. More particularly, the present invention is concerned with providing a suction apparatus for insertion into the vagina for suction and collection of the contents of the uterus into a chamber for subsequent disposal.

Diverse methods for sanitarily collecting the recurring blood and secretions flowing from the uterus of women during their child-bearing years have been devised in the past. The means proposed heretofore are either of the retaintive type or of the absorptive type. Retaintive type means are generally in the form of a cap or diaphragm which forms a dam preventing blood and secretion flow from passing from an internal organ, such as the uterus or the vagina, to the exterior of the vagina. Absorptive type means may take the form of internal absorptive devices such as tampons or plugs made of absorptive fibrous material, inserted more or less deeply into the vagina. Absorptive type means may also take the form of exterior absorptive devices, perhaps the most common type of menstrual sanitary devices, which are generally in the form of pads made of absorptive material attached to the body in some manner, and extending generally between the legs of the wearer.

All devices, of any type, present particular disadvantages. Retaintive means are prone to cause irritation and infection. They are uncomfortable and may easily be dislodged, with the result that their whole purpose is defeated and considerable embarrassment may be caused. Internal absorptive devices are often awkward to use, uncomfortable and subject to by-pass failures due to their inability to block the many folds and convolutions of the vagina in its deep section. As they are indiscriminately absorptive, they tend to dry the vaginal walls and, when disposed too close to the introitus of the vagina, they cause considerable discomfort. They are difficult to extract and when pulled through the introitus, they tend to be compressed and to regurgitate the absorbed fluids. External absorptive devices are uncomfortable to wear, bulky, non-aesthetic and non-hygenic.

The many shortcomings and inconveniences of the prior art retaintive and absorptive devices are remedied by the present invention which contemplates providing a menstrual extraction device in the form of a vaginal suction device easily operable by a woman periodically during her menstrual flow period for suctioning the contents of the uterus through the cervix. The device of the invention may be used in combination with a retaintive means in the form of a flexible cap or diaphragm, for aiding in the emptying of the uterus, or, alternatively and preferably, the device of the invention may be used once or twice a day for occasionally emptying the uterus.

During menses, shedding of the uterus inner wall causes considerable bleeding. The blood or other secretions remain contained within the uterus until excess pressure within the uterus, aided by spontaneous contractions of the uterus, causes the blood and other secretions to flow into the deep section of the vagina through the cervical os. The present invention, as a result of enabling the contents of the uterus to be periodically suctioned, facilitates release of the contents and permits the emptied uterus to fill again. After an interval of several hours, during which the uterus is again filled, such interval of time varying from person to person and being somewhat shorter at the beginning and towards the end of the menstrual period, the uterus is again emptied by use of the device of the invention. It has been discovered that the use of the device of the invention permits to eliminate the necessity of using absorptive devices altogether and, as a result of providing full evacuation of the uterus during the periodic suction operations, the result is a considerable shortening of the menstrual period. In some cases the duration of the menstrual period is shortened to a few hours only, due apparently to the suctioning of the uterus causing immediate and complete shedding of the uterus inner walls.

Devices for evacuating the contents of the uterus are known. Some devices rely on gravity for their operation, such as the catamenial appliance disclosed in U.S. Pat. No. 1,502,503, consisting of a flexible bag inserted in the vagina and provided with a tubular projection having an end inserted within the cervix, the contents of the uterus flowing by gravity into the bag. Other devices rely on suction for their operation, such as are disclosed in U.S. Pat. Nos. 3,542,031, 3,774,612, 3,769,980 and 3,804,089, which disclose uterine evacuation curettes or cannulas, having an end inserted within the cervix through the cervical os and the other connected to a source of suction. Such devices present many inconveniences, one of which is the necessity of using a speculum for enabling the insertion of the curette or cannula, and another is the requirement of considerable skill on the part of the person handling the device who, by necessity, must be a person other than the user. Another inconvenience is the risk of damaging the relatively tender tissue of the cervical os, and there is, in addition, a considerable risk of causing inflamation. These suction devices are generally designed for abortion at an early stage of pregnancy, and they suction only the interior of the uterus and not the entire vaginal cavity.

Other uterine suction devices, having no portion introduced within the cervix or uterus, are devices of the type disclosed in U.S. Pat. No. 3,860,001, generally for use during a surgical operation such as hysterectomy. These devices consist generally of a bulbous body portion insertable within and positionable in the deep part of the vagina, which are provided with large apertures through which blood and secretions are suctioned and evacuated to a container disposed exteriorly.

SUMMARY OF THE INVENTION

The present invention overcomes the inconveniences of the prior art by providing menstrual extraction by means of a simple vaginal suction device for evacuating the contents of the uterus, which can be easily operated by the user without any particular skill or outside help, and which is particularly useful in permitting a woman to dispense with the use of internal or external absorptive devices during her menstrual period. The present invention accomplishes its purposes by providing an elongated tubular member insertable in the vagina and having a screened opening registerable with the cervix and a passageway in fluid communication with a source of partial vacuum. By applying partial vacuum to the chamber formed within the tubular member and to the vaginal canal, the contents of the uterus are suctioned into the chamber. After removal from the vagina, the chamber is emptied, cleaned and sanitized, and the device is repeatedly periodically reused during the menstrual period.

BRIEF DESCRIPTION OF THE DRAWING

A better understanding of the present invention will be had by those skilled in the art when the following description of the best modes contemplated for practicing the invention is read in conjunction with the accompanying drawing wherein:

FIG. 1 is a schematic perspective view of a vaginal suction device according to the present invention;

FIG. 2 is a side elevation of a portion thereof;

FIG. 3 is a transverse section along line 3—3 of FIG. 2;

FIG. 4 is a view similar to FIG. 2 but showing a modification thereof;

FIG. 5 is a longitudinal section along line 5—5 of FIG. 3;

FIG. 6 is a view similar to FIG. 5 but showing a modification thereof;

FIG. 7 is a view similar to FIG. 2 but showing a modification thereof;

FIG. 8 is a view similar to FIG. 2 but showing a further modification thereof; and FIG. 9 is a schematic view of the device of FIGS. 1-3 in position in the vagina.

DETAILED DESCRIPTION OF THE PREFERRED EMBODIMENTS

Referring now to FIGS. 1 and 2, a menstrual extraction device according to the present invention comprises an elongated tubular member 10 connected by means of a short length of flexible tubing 12 to, for example, a hand operated vacuum aspirator 14. The hand operated vacuum aspirator 14 is of conventional design and well known in the art. Other types of vacuum aspirators may be used without departing from the spirit of the invention.

The elongated tubular member 10 has a substantially cylindrical non-collapsible body portion 16 provided with a preferably integral hemispherical front end wall 18 and a rear end wall 20. The body portion 16, which is preferably circularly cylindrical, is made with substantially rigid non-collapsible walls, and together with the integral front end wall is molded of a material such as stainless steel or preferably a plastic material. The plastic material may be opaque or transparent, as desired.

The rear end wall 20 is in the form of a disk, which may be of the same material as the body portion 16, cemented or otherwise fastened to the open end of the body portion 16. As best shown at FIG. 5, the rear end wall 20 is provided with an aperture 22 disposed in a conduit 24 attached within an appropriate bore through the end wall 20, the exteriorly projecting portion of the conduit 24 forming a fitting 26 for attaching thereover the tubing 12. In this manner, an interior chamber 28 formed within the hollow member 10 is placed in fluid communication with the vacuum aspirator 14 through the aperture 22 and the tubing 12.

The end of the body portion 16 proximate the hemispherical end wall 18 is provided with a screened opening 30 which is preferably disposed on one side of the body portion 16, and the conduit 24 is disposed through the end wall 20 out of center and proximate to the edge of the end wall corresponding to the side of the body portion 16 in which the opening 30 is formed, such that any fluid drawn into the chamber 28 during suctioning, as will be hereinafter explained, remains in the chamber 28 at a level lower than the orifice 22 such as to prevent withdrawal through the orifice 22 under normal use of the device of the invention. The opening 30 extends peripherally only about one half, at most, of the circumference of the body portion 16. The opening 30 is provided with a mesh screening 32 which in its preferred form, and as best shown at FIGS. 3 and 5, results from forming a plurality of apertures 34 disposed in a regular pattern, thus leaving between adjoining apertures 34 a lattice 36 of solid material integral with the material of the body section 16, and having rounded edges, as shown at 38 at FIG. 3.

Other types of screening may be used, such as for example forming an opening 30 on a side of the body portion 16 proximate the hemispherical end wall 18 and fitting within the opening 30, or slightly below the aperture 30 being provided with rounded edges, a screen of soft plastic material.

In use, and as shown at FIG. 9, the elongated tubular member 10 is introduced into the vagina until the hemispherical end wall 18 abuts the deepest portion of the vaginal vault. The screened aperture 30 is thus disposed opposite the cervix, as long as the tubular member 10 is properly oriented about its longitudinal axis. Proper orientation of the tubular member 10 may be indicated by way of an appropriate indexing marking and is facilitated by the excentric disposition of the tube fitting 26 being disposed angularly such as to correspond to the lateral position of the screened opening 30, as long as the user is seated or partly reclining such that the tubular member 10 is held horizontally. The vacuum aspirator is actuated and causes a drop of pressure within the chamber 28 and within the vaginal canal, thus causing in turn the contents of the uterus to be suctioned through the cervical os into the chamber 28. The labia and the muscular introitus portion of the vagina being firmly applied against the periphery of the body portion 16 proximate the end thereof projecting from the vagina insure that a firm seal is effected preventing air from the ambient from being by-passed around the peripheral surface of the body portion 16. After the uterus has been emptied, the tubular member 10 is withdrawn from the vagina, the flexible tubing is disconnected, and the contents of the chamber 28 are emptied through the opening 30. The tubular member 10 may then be washed, cleaned exteriorly and internally, and sanitized.

The present invention also contemplates that instead of a fixed end wall 20 a removable stopper 40, as shown at FIG. 6, may be used to obturate the open end portion of the body portion 16 to facilitate emptying and cleaning the chamber 28. The stopper 40 is made of plyable material such as rubber or flexible plastic, and has an excentric aperture through which is fitted the tubular member 24.

FIG. 4 illustrates a modification of the invention wherein the body portion 16 has a bulbous outer shape of slightly enlarged diameter, as shown at 42, proximate its end provided with the rear end wall 20. Such a modification of the structure, either by itself or accompanied by a series of substantially parallel annular ridges 44, provides an improved seal between the peripheral surface of the body portion 16 of the tubular member 10 and the wall of the vagina having many folds and convolutions. Alternatively, the bulbous enlarged portion 42 of the body portion 16 may be omitted, and the surface of the body portion 16 may remain smooth as illustrated at FIGS. 1 and 2, or be provided with a few annular ridges as ridges 44 formed on its outer surface.

The tubular member 10 is devoid of any sharp angles and is, as previously mentioned, made of a material, such as plastic, having a substantially smooth surface. Prior to insertion into the vagina, the tubular member 10 may be coated with a jelly or other vaginal lubricant. The edges of the apertures 34 forming the screened opening 30 are rounded such that the surface portions of the device in contact with the vagina internal walls and the cervix are incapable of causing irritation or damage. The screening 32 of the opening 30 provides a support for the cervix during suction of the vaginal canal and of the uterus contents, with the result that there is no danger or irritation or injury during repetitive use of the device of the invention in the course of a menstrual period.

Dimensionally, the tubular member 10 is within the range of approximately 18 to 35 cm in length and 3 to 4 cm in outer diameter. The screened aperture 30 is typically 4 or 5 cm in length. The apertures 34 of the screening are typically in the range of 2 to 6 mm.

The total amount of menstrual flow varies from person to person, but is normally within the range of 45–140cc. There is, therefore, ample room within the chamber 28 to contain the fluids suctioned in the chamber, without risk of overflow or of suctioning fluid into the tube 12, as long as the tubular member 10 is held substantially horizontal and the fitting or conduit 24 is correctly positioned. The configuration of FIG. 7 illustrates an example of structure wherein the main body portion 16 of the tubular member 10 is provided with an integral excentrically disposed capture chamber 46 of enlarged diameter, preferably circularly cylindrical in cross section. A removable stopper 40 is fitted in the open end of the capture chamber 46, and the conduit 24 is disposed through the stopper 40 excentrically such as to be disposed farthest away from the bottom of the capture chamber 46 when the device is in operation. Furthermore, the excentric position of the capture chamber 46 facilitates the proper orientation of the tubular member 10 about its longitudinal axis. FIG. 8 represents another modification of the device of the invention wherein the tubular member 10 is generally L-shaped, with an angled portion 48 integrally molded with the main body portion 16 of the tubular member 10 having its axis disposed at an angle relative to the longitudinal axis of the main body portion 16. The conduit 24, connectable to the flexible tubing 12, is disposed at the end of the angled portion 48 and, in use, the tubular member 10 is oriented such that the angled portion 48 projects upwardly, outside of the vagina, thus placing the suction conduit 24 away and above the level of the fluid suctioned into the tubular member 10.

Very little partial vacuum is necessary for operating the suction device of the invention. A suction of the order of magnitude of 10 to 50 cm of mercury is sufficient, and when using a vacuum aspirator pump for the purpose of providing a source of suction, a release valve set at 55–60 cm of mercury is preferably fitted to the pump to limit the partial vacuum to harmless values. It has been found that mouth-suction applied to the end of the tubing 12 is sufficient to operate the device of the invention, although it is recognized that using the mouth as a source of partial vacuum in combination with the device of the invention may be found objectionable by some users.

Although the tubular member is illustrated as having a circular periphery, it will be appreciated that it may have an oval or other peripheral shape.

Having thus described the present invention by way of typical examples of structure thereof, modifications whereof will be readily apparent to those skilled in the art, what is claimed as new is as follows:

1. A vaginal suction device comprising an elongated chamber-defining tubular hollow member for introduction into the vagina and having a substantially cylindrical non-collapsible body portion, a rounded imperforate front end wall for abutting the posterior wall of the vagina vault closing an end of said body portion, a rear end wall closing the other end of said body portion, said other end of said body portion normally projecting to the exterior of the vagina, a screened opening formed in a side of said body portion proximate said front end wall, said screened opening being engageable with the cervix of the uterus, a passageway in said rear end wall communicating with said chamber, coupling means connecting said passageway to a source of partial vacuum suctioning the contents of said uterus in said chamber, and orientation indicating means at said other end of the body portion for registering said screened opening with the cervix of the uterus, said orientation indicating means comprising said passageway and coupling means disposed proximate an edge of said rear end wall corresponding to the positioning of said screened opening in engagement with the cervix of the uterus.

2. The suction device of claim 1 wherein said body portion is substantially circularly cylindrical.

3. The suction device of claim 2 wherein said body portion has an outer bulbous shape of enlarged diameter proximate the end thereof provided with said rear end wall.

4. The suction device of claim 2 wherein said body portion has at least one peripheral annular ridge formed on the outer surface thereof proximate the end of said body portion provided with said rear end wall.

5. The suction device of claim 1 wherein said screened opening comprises a plurality of relatively small apertures disposed in a regular pattern, said apertures having substantially rounded edges.

6. The suction device of claim 5 wherein said body portion has an outer bulbous shape of enlarged diameter proximate the end thereof provided with said rear end wall.

7. The suction device of claim 5 wherein said body portion has at least one peripheral annular ridge formed on the outer surface thereof proximate the end of said body portion provided with said rear end wall.

8. The suction device of claim 1 wherein said body member and said front end wall are molded integrally of plastic material.

9. The suction device of claim 8 wherein said body portion has an outer bulbous shape of enlarged diameter proximate the end thereof provided with said rear end wall.

10. The suction device of claim 8 wherein said body portion has at least one peripheral annular ridge formed on the outer surface thereof proximate the end of said body portion provided with said rear end wall.

11. The suction device of claim 1 wherein said body portion has an outer bulbous shape of enlarged diameter proximate the end thereof provided with said rear end wall.

12. The suction device of claim 11 wherein said bulbous shaped body portion has at least one peripheral annular ridge formed on the outer surface thereof.

13. The suction device of claim 1 wherein said body portion has at least one peripheral annular ridge formed on the outer surface thereof proximate the end of said body portion provided with said rear end wall.

14. The suction device of claim 1 wherein said tubular member has a main body portion and an integral portion defining a fluid capture chamber of enlarged diameter disposed proximate said rear end wall.

15. The suction device of claim 1 wherein said tubular member has a main body portion and an integral portion defining a fluid capture chamber disposed at an angle to said main body portion proximate said rear end wall.

16. A vaginal suction device comprising an elongated tubular hollow member for introduction into the vagina and having a substantially cylindrical rigid non-collapsible body, a rounded imperforate front end wall for abutting the posterior wall of the vagina vault closing an end of said body, a rear end wall closing the other end of said body, said other end of said body normally projecting to the exterior of the vagina, a screened opening formed in a lateral portion of said body proximate said front end wall, said screened opening being positioned and dimensioned to engage with the cervix of the uterus, said screened opening having a plurality of relatively small apertures disposed in a regular pattern and having substantially rounded edges, a fluid capture chamber integrally formed in said body, a passageway in said rear end wall communicating with said chamber, coupling means connecting said passageway to a source of partial vacuum suctioning the contents of said uterus in said capture chamber and orientation indicating means at said other end of said body for registering said screened opening with the cervix of the uterus.

17. The suction device of claim 16 wherein said orientation indicating means comprises said passageway and coupling means disposed proximate an edge of said rear end wall corresponding to the positioning of said screened opening in engagement with the cervix of the uterus.

18. The suction device of claim 17 wherein said body has an outer bulbous shape of enlarged diameter proximate the end thereof provided with said rear end wall.

19. The suction device of claim 17 wherein said body has at least one peripheral annular ridge formed on the outer surface thereof proximate the end of said body portion provided with said rear end wall.

20. The suction device of claim 16 wherein said body is substantially circularly cylindrical.

21. The suction device of claim 16 wherein said body has an outer bulbous shape of enlarged diameter proximate the end thereof provided with said rear end wall.

22. The suction device of claim 16 wherein said body has at least one peripheral annular ridge formed on the outer surface thereof proximate the end of said body provided with said rear end wall.

23. The suction device of claim 16 wherein said body has an outer bulbous shape of enlarged diameter proximate the end thereof provided with said rear end wall.

24. The suction device of claim 16 wherein said fluid capture chamber is an enlarged diameter portion of said body proximate said rear end wall.

25. The suction device of claim 16 wherein said fluid capture chamber is disposed at an angle to said body proximate said rear end wall.

* * * * *